United States Patent
Glynn et al.

(10) Patent No.: US 9,968,792 B2
(45) Date of Patent: *May 15, 2018

(54) IMPLANTABLE MEDICAL DEVICE HOUSING HAVING INTEGRATED FEATURES

(71) Applicant: Heraeus Deutschland GmbH & Co. KG, Hanau (DE)

(72) Inventors: Jeremy Glynn, Buffalo, MN (US); Steven Harein, Mahtomedi, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/688,696

(22) Filed: Aug. 28, 2017

(65) Prior Publication Data

US 2018/0001093 A1  Jan. 4, 2018

Related U.S. Application Data

(62) Division of application No. 14/558,344, filed on Dec. 2, 2014, now Pat. No. 9,757,573.

(51) Int. Cl.
| | |
|---|---|
| *A61N 1/00* | (2006.01) |
| *A61N 1/375* | (2006.01) |
| *B22F 7/06* | (2006.01) |
| *B22F 7/04* | (2006.01) |
| *B22F 3/22* | (2006.01) |
| *B22F 3/105* | (2006.01) |
| *B33Y 80/00* | (2015.01) |

(52) U.S. Cl.
CPC ............. *A61N 1/375* (2013.01); *B22F 7/04* (2013.01); *B22F 7/062* (2013.01); *B22F 3/1055* (2013.01); *B22F 3/225* (2013.01); *B22F 2007/042* (2013.01); *B33Y 80/00* (2014.12)

(58) Field of Classification Search
CPC ........................................ A61N 1/375
USPC .......................... 607/36, 2, 4, 5, 9
See application file for complete search history.

(56) References Cited

U.S. PATENT DOCUMENTS

| | | | |
|---|---|---|---|
| 7,103,415 | B2 | 9/2006 | Probst et al. |
| 7,684,860 | B2 | 3/2010 | Wahlstrand et al. |
| 7,751,893 | B2 | 7/2010 | Biggs, Jr. et al. |
| 7,853,324 | B2 | 12/2010 | Stevenson et al. |
| 8,005,539 | B2 | 8/2011 | Burnes et al. |

(Continued)

OTHER PUBLICATIONS

Restriction Requirement for U.S. Appl. No. 14/558,344 dated Jul. 7, 2016 (7 pgs).

(Continued)

*Primary Examiner* — Matthew W Ing
(74) *Attorney, Agent, or Firm* — Dicke, Billig & Czaja, PLLC

(57) ABSTRACT

One aspect is a housing for an implantable medical device, including first housing portion of metal, an intermediate portion of metal and having first and second sides opposite one another and having integrated features, and a second housing portion of metal. The first housing portion is sealed to the first side of the intermediate portion and the second housing portion is sealed to the second side of the intermediate portion thereby forming an housing internal space within first and second housing portions and containing the intermediate portion and its features, such that the features are hermetically sealed within the housing relative to an external space that is outside the housing.

15 Claims, 8 Drawing Sheets

(56) References Cited

U.S. PATENT DOCUMENTS

| | | |
|---|---|---|
| 8,380,311 B2 | 2/2013 | Li et al. |
| 8,473,056 B2 | 6/2013 | Engmark et al. |
| 8,562,706 B2 | 10/2013 | Siber |
| 9,757,573 B2 | 9/2017 | Glynn et al. |
| 2012/0193141 A1 | 8/2012 | Reisinger et al. |
| 2016/0157371 A1 | 6/2016 | Glynn et al. |

OTHER PUBLICATIONS

Office Action for U.S. Appl. No. 14/558,344 dated Dec. 12, 2016 (8 pgs).
Notice of Allowance for U.S. Appl. No. 14/558,344 dated May 5, 2017 (8 pgs).
Office Action for U.S. Appl. No. 15/688,729 dated Oct. 31, 2017 (5 pgs).

IMPLANTABLE MEDICAL DEVICE HOUSING HAVING INTEGRATED FEATURES

CROSS-REFERENCE TO RELATED APPLICATIONS

This application is a divisional of U.S. patent application Ser. No. 14/558,344, entitled "IMPLANTABLE MEDICAL DEVICE HOUSING HAVING INTEGRATED FEATURES," having a filing date of Dec. 2, 2014, and which is incorporated herein by reference.

BACKGROUND

There is constant pressure in the marketplace for implantable medical devices to be physically smaller in size. Currently, manufacturing methods for housings of implantable medical devices are machining, stamping, or super plastic forming. Each method has limitations. With stamping, two housing portions are formed and then joined together to form the complete housing. It is not possible with stamping, however, to produce housing portions that include separate cavities or features integrated into the housing portion. Stamping also requires uniform wall thickness throughout the part. As such, battery and capacitor assemblies must be built as separate items and added into the housing portions.

Superplastic forming (SPF) also is a very challenging method of producing housing components and also has limitations in producing housing portions that include separate cavities or features integrated into the housing portion. The SPF process is very slow, and has significantly more variation in dimensions of part features.

For these and other reasons there is a need for the embodiments of the present disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
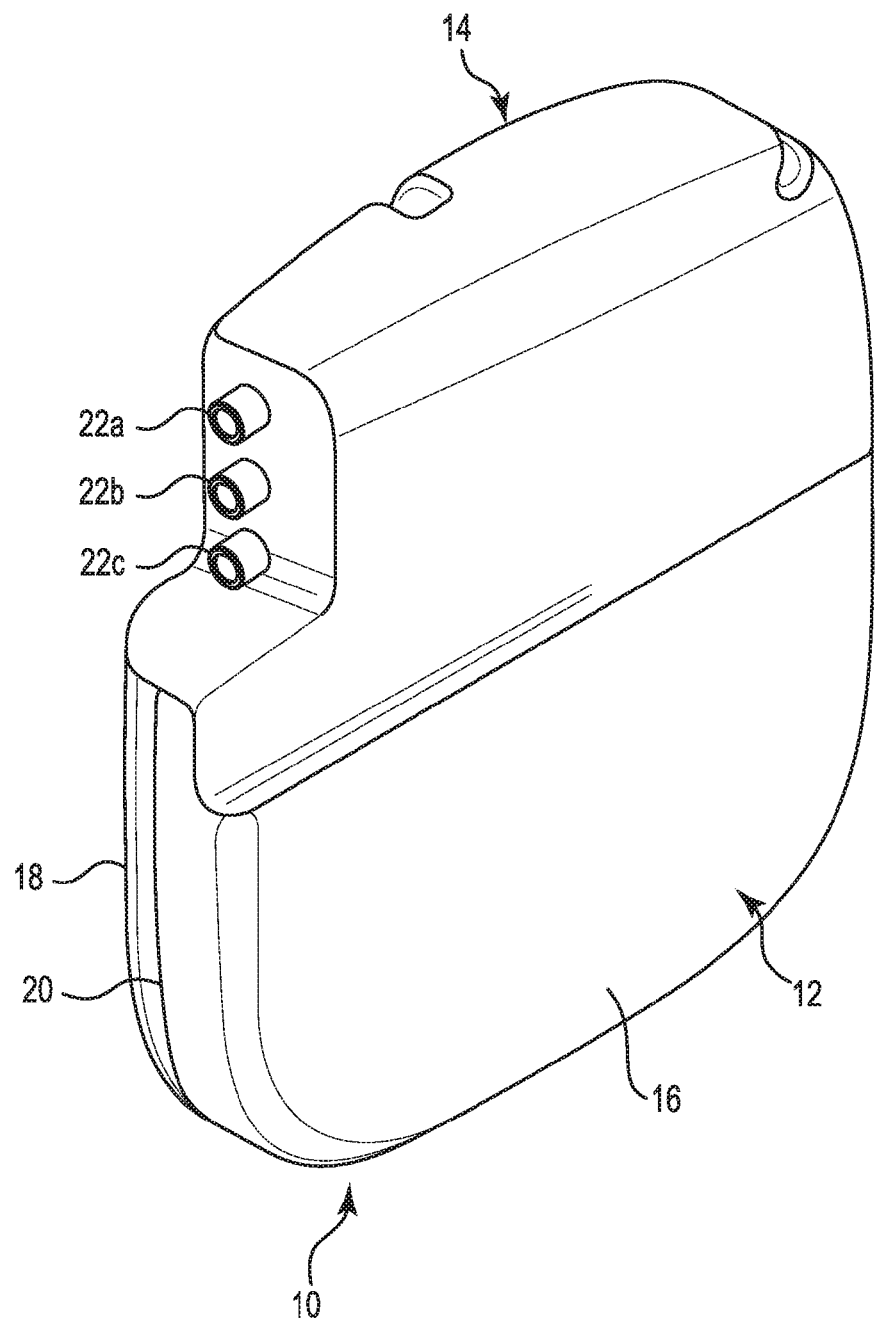
FIG. 1 illustrates a perspective view of an implantable medical device in accordance with one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In one embodiment, a housing for an implantable medical device includes a first housing portion of metal and having features integrated in the first housing portion and a second housing portion also of metal. The first and second housing portions are sealed together thereby forming the housing with an internal space that is within first and second housing portions and that fully contains the features and component cavity such that they are hermetically sealed relative to an external space outside the housing.

By directly integrating features into the first housing, overall space is saved in the device, the weight of the device is decreases, the required assembly steps for the device decrease, stocking requirements for separate components is reduced and overall costs are reduced.

In one embodiment, the first and second housing portions each include walls configured about each respective periphery and are configured immediately adjacent each other on the housing at a connection line such that the first and second housing portions are readily joined along the connection line. Accordingly, the housing portions are easy to weld together, because the connection line is easily accessed on the outside of the housing and can be readily welded.

In one embodiment, the features of housing include walls, ribs, component cavities, standoffs, recesses, knuckles, and back-up bands. In one case, the features comprise ribs extending from the first housing portion, the walls and the ribs together defining a component cavity configured to receive components for the medical device. Such features provide numerous advantages, such as allowing for assembly of device components directly into the housing portion without a separate housing, increased automation of the assembly process of implantable medical device, and the potential of being produced as a single piece flow assembly within a continuous flow assembly line.

In one embodiment, the component cavity substantially contains materials for at least one of a capacitor and a battery and is characterized in that neither the capacitor nor the battery has an independent housing separate from the first housing portion. In one case, the ribs further include a step surrounding the component cavity that is configured to receive a lid, the ribs and step all integrally formed with the first housing portion, and the lid sealing the capacitor or the battery. The component cavity without separate housing avoids duplication of housings, thereby allowing for a smaller and lighter overall device. It avoids forming separate components, thereby reducing component inventory, reducing exposure to quality-control issues, and lowering overall product cost.

In one embodiment, the housing includes an intermediate portion between the first and second housing portions, the intermediate portion defining a first chamber between the first housing portion and the intermediate portion and a second chamber between the second housing portion and the intermediate portion. In one case, the first and second housing portions and intermediate portion each include wall sections configured about each respective periphery and configured immediately adjacent each other on the housing, the wall sections of the first housing portion and the intermediate portion forming a first connection line and the wall sections of the second housing portion and the intermediate portion forming a second connection line. In one embodiment, the portions are readily joined along the first and second connection lines. This configuration creates separate chambers that may be useful in separating components of the medical device, and the materials of the components, so that they can be kept separate. Also, the connection lines allow for easy access to weld all the portions together.

In one embodiment, the intermediate portion includes a back-up band adjacent one of the first and second connection lines, the back-up band configured to protect components within the housing when the housing is welded along the first or second connection lines.

In one embodiment, the first and second housing portions are Ti 6Al-4V (Grade 5 titanium), Ti 6Al-4V ELI (Grade 23 titanium), or Ti 3Al 2.5V (Grade 9 titanium). These materials provide advantages in some applications, because of their favorable thermal properties.

In one embodiment, a housing for an implantable medical device includes a first housing portion of metal, an intermediate portion of metal and having first and second sides opposite one another and having integrated features, and a second housing portion of metal. The first housing portion is sealed to the first side of the intermediate portion and the second housing portion is sealed to the second side of the intermediate portion thereby forming an housing internal space within first and second housing portions and containing the intermediate portion and its features, such that the features are hermetically sealed within the housing relative to an external space that is outside the housing.

By directly integrating features into the first housing, overall space is saved in the device, the weight of the device is decreases, the required assembly steps for the device decrease, stocking requirements for separate components is reduced and overall costs are reduced.

In one embodiment, the features include walls, ribs, component cavities, standoffs, recesses, knuckles, or back-up bands. Such features provide numerous advantages, such as allowing for assembly of device components directly into the housing portion without a separate housing, increased automation of the assembly process of implantable medical device, and the potential of being produced as a single piece flow assembly within a continuous flow assembly line.

In one embodiment, the intermediate portion defines a first chamber between the first housing portion and the intermediate portion and a second chamber between the second housing portion and the intermediate portion. The separate chambers may be useful in separating components of the medical device, and the materials of the components, so that they can be kept separate.

In one embodiment, the first and second housing portions and intermediate portion each comprise wall sections configured about each respective periphery and configured immediately adjacent each other on the housing, the wall sections of the first housing portion and the intermediate portion forming a first connection line and the wall sections of the second housing portion and the intermediate portion forming a second connection line, wherein the portions are readily joined along the first and second connection lines. Accordingly, the housing portions are easy to weld together, because the connection line is easily accessed on the outside of the housing and can be readily welded.

In one embodiment, the intermediate portion includes a back-up band adjacent one of the first and second connection lines, the back-up band configured to protect components within the housing when the housing is welded along the first or second connection lines.

In one embodiment, the first and second housing portions and intermediate portion are Ti 6Al-4V (Grade 5 titanium), Ti 6Al-4V ELI (Grade 23 titanium), or Ti 3Al 2.5V (Grade 9 titanium). These materials provide advantages in some applications, because of their favorable thermal properties.

In one embodiment, a method of fabricating a housing for an implantable medical device, includes forming a first housing portion comprising metal using an additive manufacturing process such that features are integrated into the first portion, forming a second housing portion comprising metal, and joining the first and second housing portions thereby sealed an internal space of the housing within first and second portions and fully containing the features such that they are hermetically sealed relative to an external space outside the housing.

By directly integrating features into the first housing, overall space is saved in the device, the weight of the device is decreases, the required assembly steps for the device decrease, stocking requirements for separate components is reduced and overall costs are reduced.

In one embodiment, the additive manufacturing process includes at least one of metal injection molding (MIM), direct metal laser sintering (DMLS), stereolithography (SLA), and three-dimensional printing (3D printing). Each of these processes advantageously allow forming of metal portions, which include the advantageous features that are contained within the housing, without requiring any further processing of the metal housing portions after the are formed.

In one embodiment, the method includes forming an intermediate portion comprising metal using an additive manufacturing process such that features are integrated into the intermediate portion. In one case, joining the first and second housing portions further includes joining the intermediate portion between the first and second housing such that features of the intermediate portion are contained in the interior of the housing. The intermediate portion defines separate chambers that may be useful in separating components of the medical device, and the materials of the components, so that they can be kept separate.

In one embodiment, forming the first housing portion includes forming a component cavity configured for holding materials of at least one component for the medical device. In one case, materials of at least one component for the medical device are assembled into the component cavity and the component cavity is sealed. The at least one component has no housing other than the component cavity.

By directly integrating features into the first housing, overall space is saved in the device, the weight of the device is decreases, the required assembly steps for the device decrease, stocking requirements for separate components is reduced and overall costs are reduced.

FIG. 1 illustrates a perspective view of implantable medical device 10 in accordance with one embodiment. Implantable medical device 10 includes housing 12 and header 14. Housing 12 includes a first housing portion 16 and a second housing portion 18, which are coupled together in a sealed manner along connecting line 20.

In one embodiment, header 14 is mounted onto housing 12 in any of a variety of means. For example, header 14 can be adhered to housing 12 using an appropriate implantable grade epoxy bonding material. In one embodiment, header 14 is a molded elastomeric material, molded plastic, molded urethane, or the like.

Implantable medical device 10 may be any of a variety of therapeutic devices, including cardiac pacemakers or defibrillators. In such devices, housing 12 is configured with electronic circuitry that is hermetically sealed within the interior of housing 12 relative to its exterior. This electronic circuitry is coupled to bores within header 14, which in turn correspond with one or more connectors 22a/22b/22c. Leads (not illustrated), such as cables, can be connected to the implantable medical device 10 via the header 14, connectors 22a/22b/22c and bores. For example, proximal ends of the leads can respectively be inserted into connectors 22a/22b/22c and bores, while the distal ends of the leads can be coupled to electrodes that are surgically secured to body tissue. Signals can then be sent to and/or received from the body tissue.

Accordingly, when implantable medical device 10 is implanted within a body, such as within a human body, electronic circuitry hermetically sealed within housing 12 can be in communication with tissue within the body where electrodes are placed. Such electronic circuitry can then sense signals at the tissue and/or deliver signals to the tissue through the leads coupled within connectors 22a/22b/22c.

In one embodiment, first housing portion 16 and second housing portion 18 each metallic and are individually formed and then secured together with a hermetic seal along connecting line 20. For example, the first and second housing portions 16/18 are a biocompatible metal, such as titanium or platinum, and are welded together, such as via laser welding, along connecting line 20, to both seal and attach the portions. Alternatively, the first and second housing portions 16/18 can be adhered to each other using an appropriate implantable grade epoxy bonding material, for example.

With prior designs, first and second housing portions 16/18 were stamped or superplastic formed. As such, prior designs have relatively smooth wall surfaces without features. First and second housing portions 16/18 in accordance with present embodiments, however, are formed using additive manufacturing processes, such as metal injection molding (MIM), direct metal laser sintering (DMLS), stereolithography (SLA), or three-dimensional printing (3D printing). Accordingly, first and second housing portions 16/18 in accordance with present embodiments are formed having a variety of features that are integrally formed with the first and second housing portions 16/18. There integral features have numerous advantages that will be fully discussed below.

FIGS. 2A-2D illustrate views of first housing portion 16 in accordance with one embodiment. In the figures, first housing portion 16 is illustrated apart from second housing portion 18 such that inner surface 17 of first housing portion 16 is visible in the figures. First housing portion 16 includes outer wall 30, first rib portion 32, second rib portion 34, third rib portion 36, and fourth rib portion 38. Each of first-fourth rib portions 32-38 extend out from inner surface 17 such that there are fully contained and hermetically sealed within housing 12 when first and second housing portions 16/18 are sealed together.

Outer wall 30 extends out from inner surface 17 about the periphery or perimeter of first housing portion 16. In one embodiment, outer wall 30 meets a mirror-image wall on second housing portion 18 at connecting line 20, where the two portions 16/18 are sealed together as discussed above. First-fourth rib portions 32-38 within outer wall 30 comprise features that are useful for implantable medical device 10.

In one embodiment, first rib portion 32 extends between two locations of outer wall 30, thereby defining a first component cavity 40. First component cavity 40 is bounded by surface 17 on its bottom (as first housing portion 16 is oriented in FIG. 2A), and bounded around all sides by the combination of wall 30 and rib 32. Similarly, second and third rib portions 34 and 36 extend between two locations of outer wall 30, thereby defining a second component cavity 42 bounded by surface 17, wall 30 and ribs 34 and 36. In one embodiment, first and second cavities 40 and 42 can be specifically configured to contain components of implantable medical device 10, such as batteries and capacitors. For example, outer wall 30 and first rib portion 32, which form first component cavity 40, can be configured such that the shape of first component cavity 40 substantially matches the shape of a battery to be used in implantable medical device 10. Accordingly, a battery may be readily placed within first component cavity 40 and then easily sealed. Furthermore, as will be discussed more fully below, cavities 40 and 42 can be configured to substantially contain the materials that make up components or devices, such as batteries and capacitors, such that these components or devices can be assembled in place without requiring a separate housing.

Figure 2A:
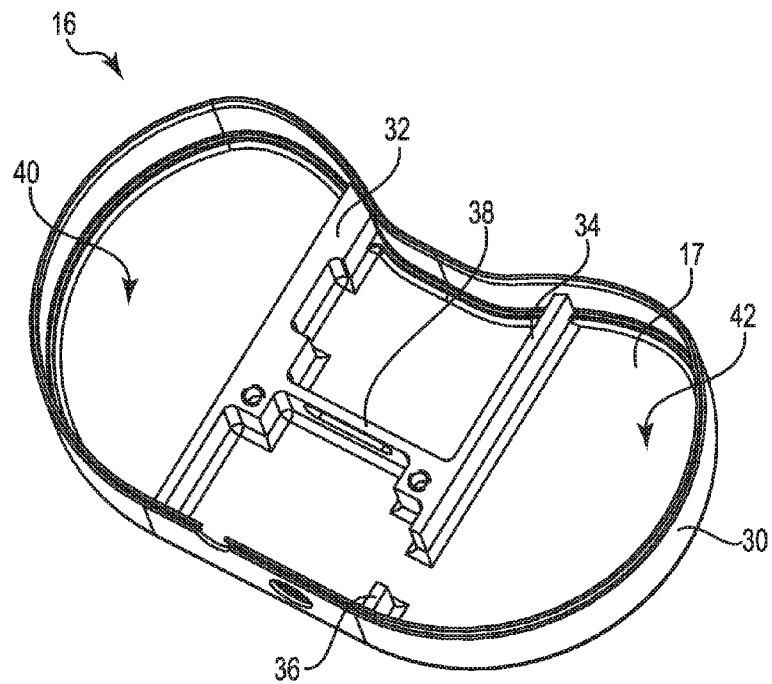
FIG. 2A illustrates a top perspective view of a housing portion in accordance with one embodiment.
Figure 2B:
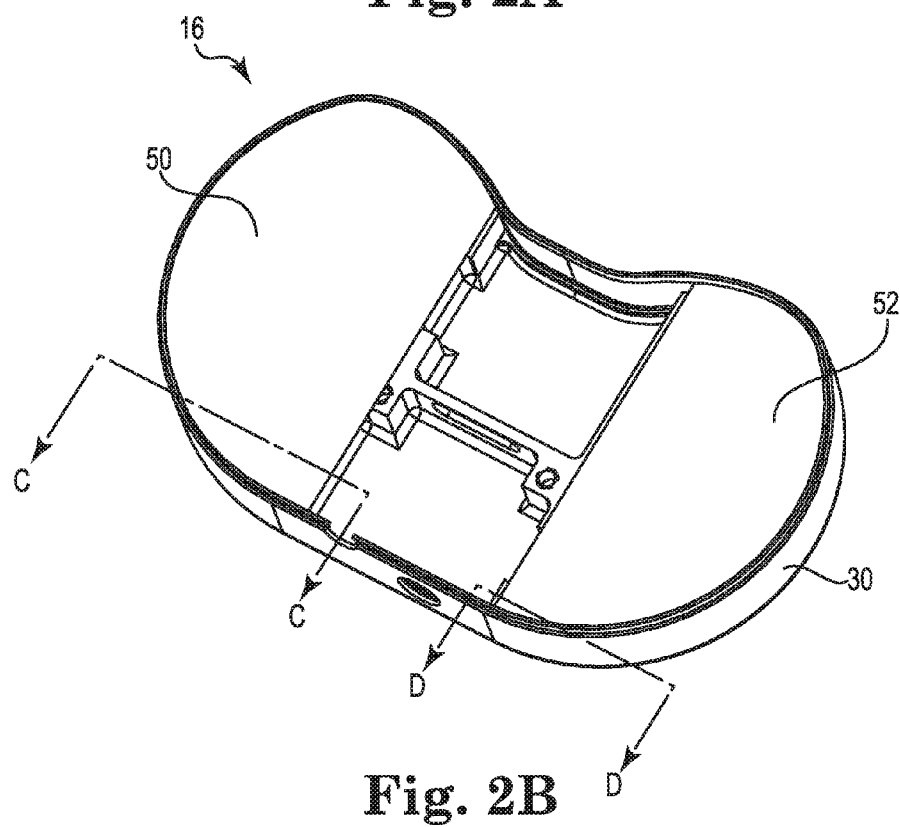
FIG. 2B illustrates a top perspective view of a housing portion including covers in accordance with one embodiment.

FIG. 2B illustrates a top perspective view of first housing portion 16 with first cover 50 in place over first component cavity 40, thereby sealing a component, such as a battery, within first component cavity 40. In some applications, it is useful if a battery is hermetically sealed within first component cavity 40. As such, forming first housing portion 16 with outer wall 30 and first rib portion 32 such that the battery is fully contained within first component cavity 40, allows the battery to be hermetically sealed within first component cavity 40 by simply sealing first cover 50 in place over first component cavity 40.

Furthermore, prior designs, where housing portions are stamped or SPF and accordingly do not have features such as ribs 32, required a that a component, such as a battery, be a fully contained component with its own housing that is then attached otherwise fixed within the implantable housing. With first housing portion 16, however, first component cavity 40 is specifically configured such that materials of a battery can be assembled directly into first component cavity 40, without the battery requiring its own separate housing.

Figure 2C:
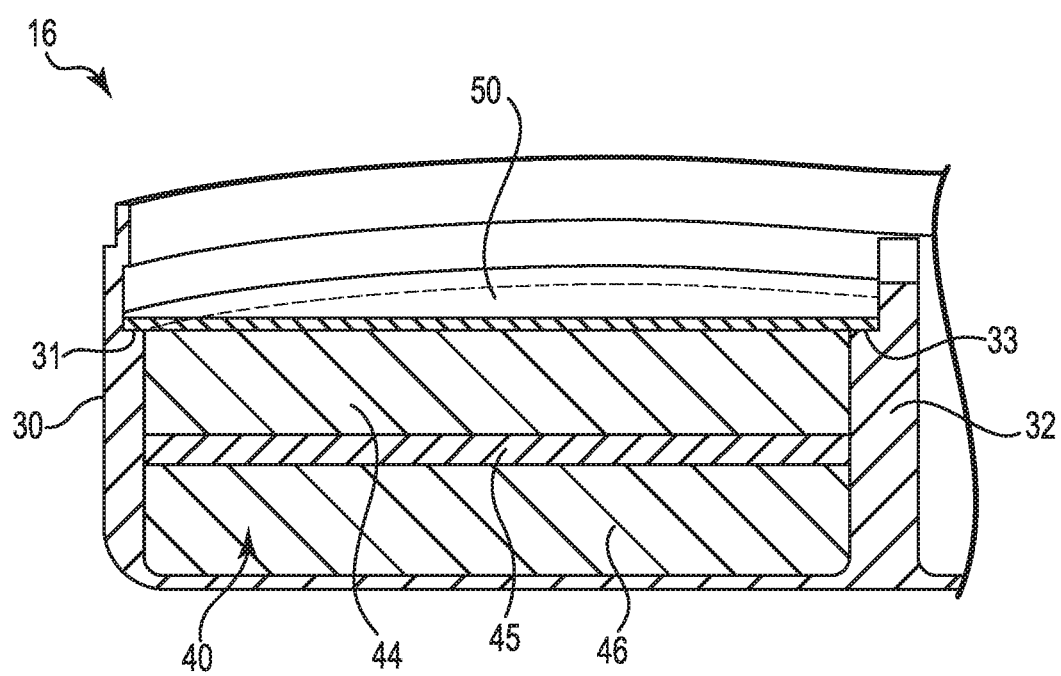
FIG. 2C illustrates a cross-sectional view, taken alone line C-C in FIG. 2B, of a first housing portion in accordance with one embodiment.

FIG. 2C illustrates a cross-sectional view, taken alone line C-C in FIG. 2B, of first housing portion 16 illustrating first component cavity 40 fully containing the materials of a battery in accordance with one embodiment. In one embodiment, cathode material 46 is placed within first component cavity 40, then a separator material 45 is placed over it, and an anode material 44 is placed over the separator material 45. Once materials 44/45/46 are assembled into place, lid 50 is then welded in place over them, thereby sealing the materials within first component cavity 40. In one embodiment, the seal is hermetic. Cathode material 46 and anode material 44 can then be electrically coupled to electronics with implantable medical device 10 such that the combined materials 44/45/46 within first component cavity 40 function as a battery for implantable medical device 10.

In the illustration of FIG. 2C, cathode material 46, separator material 45, and an anode material 44 are illustrated as metallic materials, such as a lithium metal for anode material 44 and iodine, manganese oxide, carbon monofluoride, and silver vanadium oxide for cathode 46. A variety of other material configurations may also be readily assembled within first component cavity 40. For example, thin film lithium ion battery materials having a substrate, electrolyte, current collector, anode, cathode, and a separator can also be assembled within first component cavity 40.

Also, various other known materials, including liquid forms thereof, are also readily contained within first component cavity 40. Because first component cavity 40 is substantially surrounded, on its lower side by surface 17 and bounded around its entire periphery by the combination of wall 30 and rib 32, it readily holds and contains any of a variety of materials that can be combined to function as a battery, and keep them isolated from the remaining interior of housing 12. But, instead of requiring that these materials be separately packaged in an independent and separate battery housing, first housing portion 16, with its features such as wall 30, and rib 32, provides an effective housing for the battery. Accordingly, by foregoing need for a separate battery housing, first housing portion 16 saves space in the device 10, decreases weight of the device 10, decreases required assembly and stocking of a separate component and reduces cost.

In one embodiment, outer wall 30 is further configured with step 31 at its upper side and first rib portion 32 is likewise configured with step 33 at its upper side. Steps 31 and 33 together substantially surround the perimeter of first component cavity 40 such that first cover 50 can be configured as a simple flat piece of metal with a profile shaped to match the profile of first component cavity 40 and fit snuggly over first component cavity 40. First cover 50 can be placed onto steps 31 and 33 after the battery is assembled in place, and then welded around its periphery to hermetically seal the battery within first component cavity 40.

Because first housing portion 16 is formed via additive manufacturing processes, such MIM, DMLS, SLA, or 3D printing, outer wall 30 and first rib portion 32, including steps 31 and 33, are all integrally formed as part of forming first housing portion 16. As such, assembly of implantable medical device 10 is greatly simplified. After first housing portion 16 is formed, the materials for a battery are assembled into first component cavity 40, which was formed as part of the process of forming first housing portion 16. Next, the battery materials are sealed by simply placing first cover 50 along steps 31 and 33, which were also formed as part of the process of forming first housing portion 16. Then cover 50 is welded into place thereby hermetically sealing the battery.

When a housing portion is stamped or superplastic formed, any defined areas for placing and sealing components such as materials for a battery must to added to the housing portion using post-processing techniques after the housing portion has been formed. This adds to the cost and time of the process of assembling a medical device.

Furthermore, integrally forming features, such as first rib portion 32, including steps 31 and 33 into first housing portion 16 allows for increased automation of the assembly process of implantable medical device 10. For example, first rib portion 32 and outer wall 30 create a well-defined periphery for first component cavity 40 such that an automated placement device can place readily place the materials of a battery within first component cavity 40 without a human operator intervening. Similarly, since the combination of steps 31 and 33 creates a ridge the completely surrounds first component cavity 40, an automated placement device can also readily place first cover 50 over first component cavity 40 and within the defined ridge without a human operator intervening. This increases the speed of assembly and reduces the costs.

Furthermore, by integrating first and second component cavities 40 and 42 directly into the fabrication of first and/or second housing portions 16/18, the entire volume of implantable device 10 is reduced. In prior designs, independent housings for holding the materials of components such as a battery or capacitor are required. Because these components are assembled independently, they have their own housing so that the components can be transferred and stored in preparation for adding them later to a housing as it is assembled. With such designs, a first wall of the housing portion of the implantable medical device is required, and a second wall is required for an independent housing that is configured to hold the battery, capacitor or other component. Because the battery and capacitor components in accordance with the present embodiment are assembled directly into a component cavity defined by common walls with the housing portion 16, the overall size of implantable device 10 is reduced.

Accordingly, in one embodiment the entire implantable device 10 has the potential of being produced as a single piece flow assembly within a continuous flow assembly line. Rather than being formed as separate components, as in prior designs, battery and capacitor subassemblies are formed right into component cavities that are integral in the housing portion 16, thereby reducing component inventory, reducing exposure to quality-control issues, and lowering overall product cost.

Additive manufacturing processes, such MIM, DMLS, SLA, or 3D printing, also affords implantable device designers more design freedom than what is available with conventional stamping. With additive manufacturing of housing portions, features such as threaded embossments, varying wall thicknesses, stepped edges and ribs can all be incorporated into the design. This leads to fewer number of components required for these types of products and overall smaller device sizes when compared to conventional stamping methods.

In addition, conventional designs of housings for implantable enclosures, which are produced with stamping or SPF techniques, are typically limited to using commercially pure titanium (CP Ti) (typically, Grade 1-2 titanium). The mechanical properties of CP Ti make it conducive for conventional manufacturing methods of stamping or deep drawing the material to certain geometry. Also, alloys other than CP Ti are seldom specified for implantable enclosures, because it is very challenging, and in some cases impossible, to produce an enclosure with other titanium alloys in an economical manner.

However, with additive manufacturing processes, such MIM, DMLS, SLA, or 3D printing, in accordance with several embodiments, use may be made of different titanium alloys, such as Ti 6Al-4V (Grade 5 titanium) Ti 6Al-4V ELI (Grade 23 titanium) or Ti 3Al 2.5V (Grade 9 titanium). Because Grade 5 and Grade 9 titanium has certain thermal properties and other advantages over Grade 1 or 2 titanium, it would be useful in some applications to employ a housing with Grades 5, 9, 23 titanium, or other. Using technologies of additive manufacturing, allows more design freedom for implantable device 10, because these technologies are conducive to producing enclosures with the different titanium alloys listed. The device designer would have the design freedom to even specify CP Ti on certain sections of the device and one of the Ti alloys on another section, depending on the type of manufacturing method being used to produce the part.

Using additive manufacturing processes to form first and second housing portions 16 and 18, including various features therein, can include a variety of configurations in accordance with various embodiments. For example, as illustrated in FIG. 2A, the combination of outer wall 30 and second and third rib portions 34 and 36 also define second component cavity 42. Second component cavity 42 can be used similarly to the above-described first component cavity 40. For example, second cover 52 (illustrated in FIG. 2B) can be welded over second component cavity 42 in order to seal in components of implantable medical device 10, such as a capacitor. In one embodiment, outer wall 30 and second and third rib portions 34 and 36, which surround the periphery of second component cavity 42, are configured with step features such as described above with respect to first component cavity 40. In this way, second cover 52 fits readily over second component cavity 42 and is readily welded into place.

In addition, because second and third rib portions 34 and 36 are spaced apart slightly, the space between them can be used to accommodate connections between the components within second component cavity 42 and those outside it. A sealed feedthrough (as will be discussed in additional detail below) can be located in the space between second and third rib portions 34 and 36 to fill it in, such the electrical communication is provided between the interior and exterior of second component cavity 42, but also sealing off the opening so that hermeticity is still maintained between the interior and exterior of second component cavity 42.

Figure 2D:
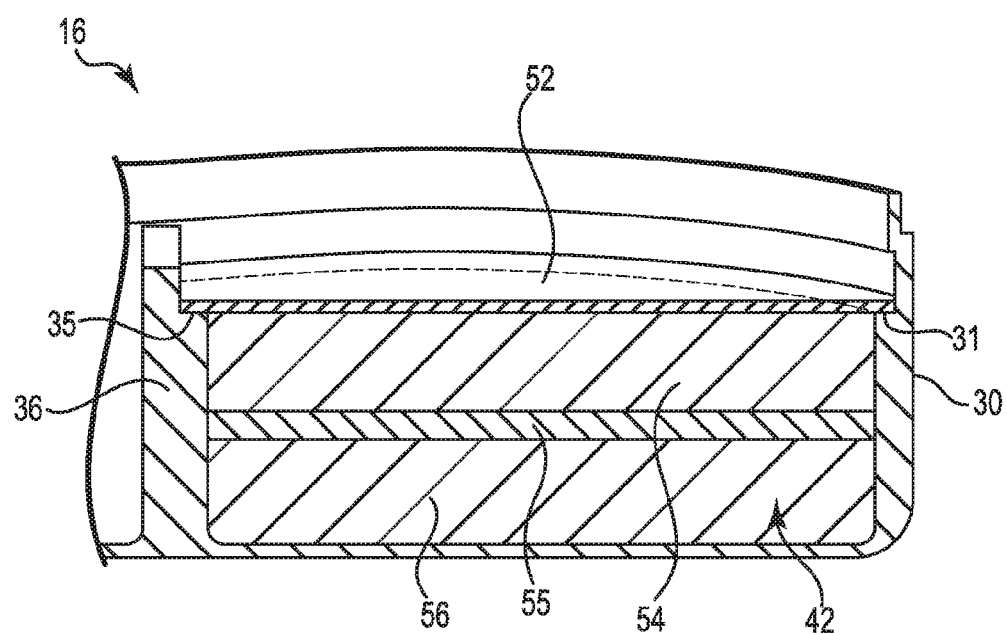
FIG. 2D illustrates a cross-sectional view, taken alone line D-D in FIG. 2B, of a first housing portion in accordance with one embodiment.

FIG. 2D illustrates a cross-sectional view, taken alone line D-D in FIG. 2B, of first housing portion 16 illustrating second component cavity 42 containing the materials of a capacitor in accordance with one embodiment. In one embodiment, first conductive plate 56 is placed within second component cavity 42, then a dielectric material 55 is placed over it, and a second conductive plate 54 is placed over the dielectric material 55. Once plates 56 and 54 and dielectric 55 are assembled into place, lid 52 is then welded in place over them, thereby sealing the materials within second component cavity 42. In one embodiment, the seal is hermetic. First and second plates 56 and 54 can then be electrically coupled to electronics with implantable medical device 10 such that the combined materials 54/55/56 within second component cavity 42 function as a capacitor for implantable medical device 10.

In the illustration of FIG. 2D, first conductive plate 56, dielectric material 55 and second conductive plate 54 are illustrated as a simplified example of a capacitor that can be used in implantable medical device 10. Various other configurations and materials may be readily used as well.

Because second component cavity 42 is substantially surrounded, on its lower side by surface 17 and bounded around its entire periphery by the combination of wall 30 and ribs 34 and 36, it readily holds any of a variety of materials that can be combined to function as a capacitor. But, instead of required that these materials be separately packaged in a capacitor housing, first housing portion 16, with its features such as wall 30, and ribs 34/36, provides an effective housing for the capacitor. Accordingly, by foregoing need for a separate capacitor housing, first housing portion 16 saves space in the device 10, decreases weight of the device 10, decreases required assembly and stocking of a separate component and reduces cost.

As also illustrated in FIG. 2A, added manufacturing processes allow for housing portions 16 and/or 18 to have additional cavities and other defined areas with additional features, such as fourth rib portion 38. Furthermore, other configurations and shapes for rib portions, cavities, defined sections and other features of housing portions are possible.

Figure 3A:
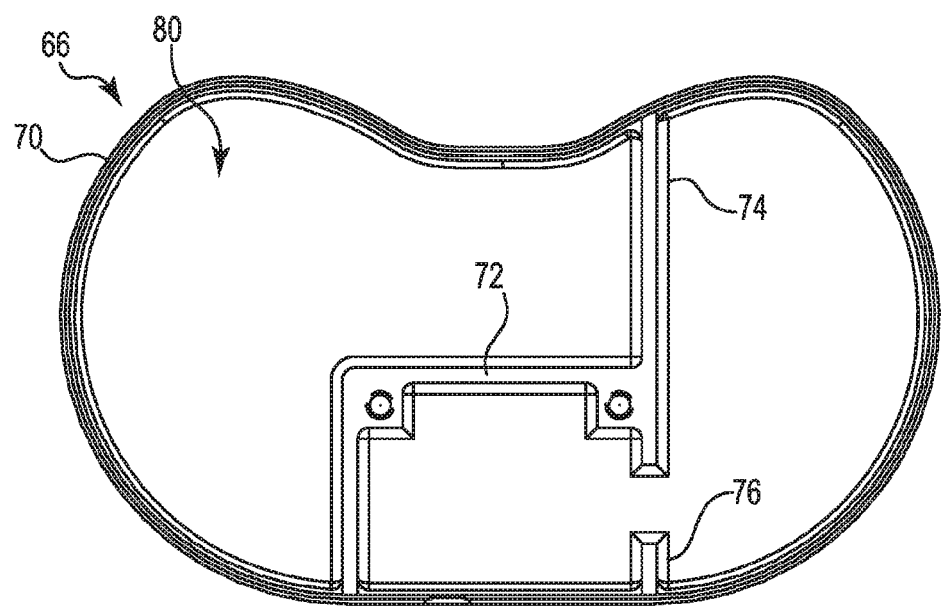
FIG. 3A illustrates a top perspective view of a housing portion in accordance with one embodiment.
Figure 3B:
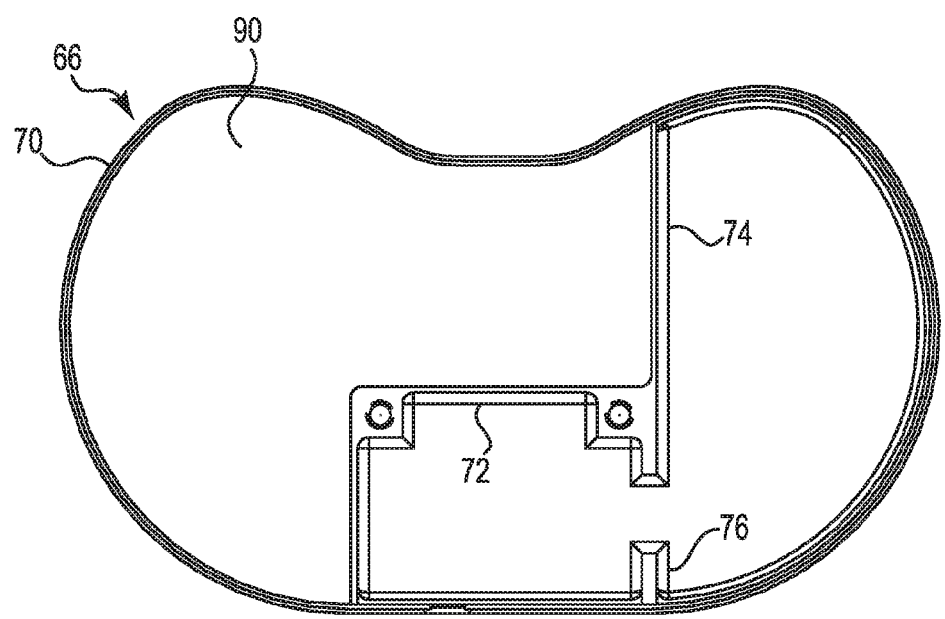
FIG. 3B illustrates a top perspective view of a housing portion including a cover in accordance with one embodiment.

For example, FIGS. 3A and 3B illustrate views of housing portion 66 in accordance with one embodiment. In the figures, housing portion 66 is illustrated as a single portion apart from a complementary housing portion, such as first and second housing portions 16 and 18 discussed above and illustrated in FIGS. 2A-2D. Housing portion 66 includes features such as outer wall 70, first rib portion 72, second rib portion 74, and third rib portion 76. Each of first-third rib portions 72-76 extend from an inner surface of housing portion 66 such that there are fully contained and hermetically sealed within a housing once housing portion 66 is sealed against a complementary housing portion.

As illustrated in FIGS. 3A and 3B, a variety of configurations and shapes are possible for features of housing portion 66. In one embodiment, first rib portion 72 is an L-shaped portion extending from outer wall 70 on one end to second rib portion 74 on its other end, thereby defining component cavity 80. As is evident, component cavity 80 has a shape on one side that follows the L-shaped portion of first rib portion 72 and a shape on its other side that follows the outline of wall 70. Accordingly, component cavity 80 can accommodate the assembly of more components and/or larger components than can first component cavity 40 described above.

Furthermore, each of outer wall 70 and first rib portion 72 can be configured with steps substantially surrounding the periphery of component cavity 80, such as illustrated and discussed previously with respect to first component cavity 40. Accordingly, cover 90 can be provided with a profile to match component cavity 80, as illustrated in FIG. 3B, such that cover 90 is readily placed over component cavity 80 within the ridge formed by the stepped portions of outer wall 70 and first rib portion 72. Once in place, cover 90 can be welded around its perimeter in order to hermetically seal component cavity 80 in one embodiment.

Figure 4A:
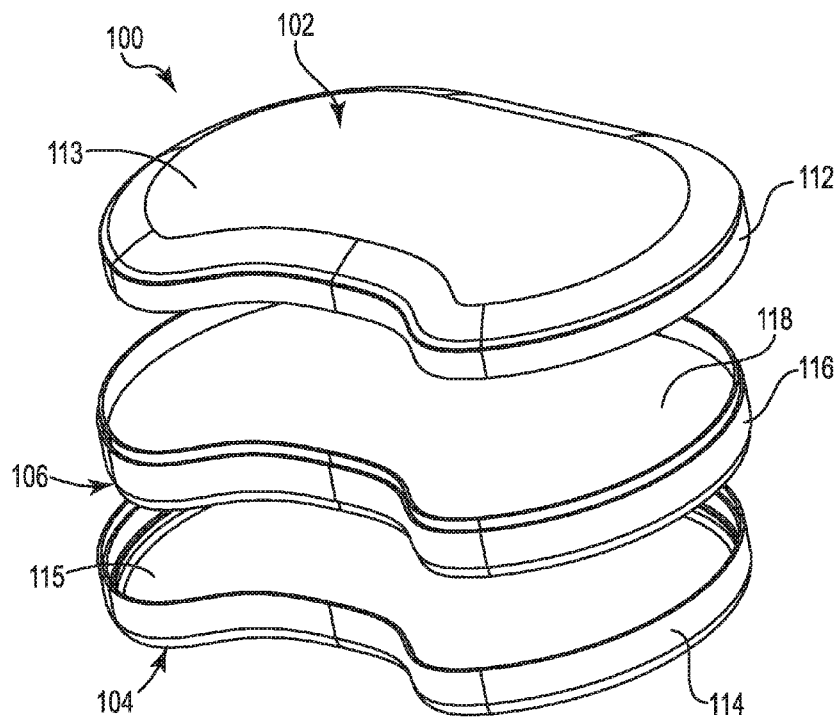
FIG. 4A illustrates an exploded view of a housing for an implantable medical device in accordance with one embodiment.
Figure 4B:
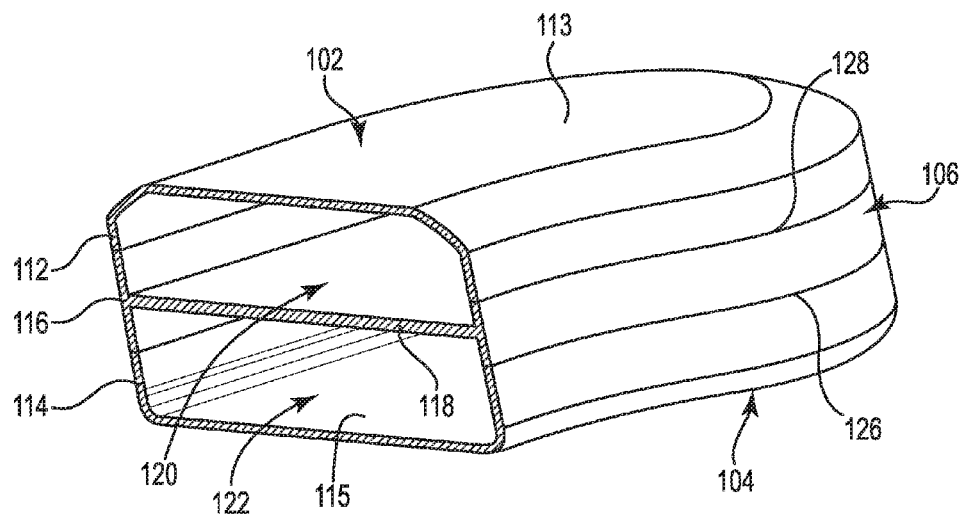
FIG. 4B illustrates a sectional view of a housing for an implantable medical device in accordance with one embodiment.

FIGS. 4A-4B illustrate a housing 100 for an implantable medical device in accordance with one embodiment. Housing 100 includes first housing portion 102, second housing portion 104 and intermediate portion 106. In one embodiment, intermediate portion 106 is positioned between first and second housing portions 102 and 104, such that when first housing portion 102 is sealed to a first intermediate portion 106 on a first side and second housing portion 104 is sealed to a first intermediate portion 106 on a second side opposite the first, the inside of housing 100 is fully hermetically sealed relative to its outside. Furthermore, in one embodiment intermediate portion 106 divides housing 100 internally into two separate chambers.

In one embodiment, first housing portion 102 includes main surface 113 and wall 112 extending therefrom, second housing portion 104 includes main surface 115 and wall 114 extending therefrom, and intermediate portion 106 includes main surface 118 and wall 116 extending therefrom. Although FIG. 4A is an exploded view, when housing 100 is fully assembled and sealed together, wall 112 is sealed to wall 116 along its upper edge (as oriented in FIG. 4A) and wall 114 is sealed to wall 116 along its lower edge (as oriented in FIG. 4A). This defines a first inner chamber 120 between main surfaces 113 and 118 and a second inner chamber 122 between main surfaces 115 and 118, as illustrated in the cross-sectional view of FIG. 4B.

In one embodiment, first and second chambers 120 and 122 are separated by intermediate portion 106, and specifically by main surface 118, such that chambers 120/122 are hermetically sealed relative to one another. This may be useful in a variety of applications where one or more components, or the materials of one or more components, in one of the chambers 120/122 need to be isolated from components in the other chamber. For example, in one embodiment electronics can be placed in first chamber 120, while a battery and/or a capacitor can be assembled in second chamber 122, such that the electronics of the medical device 10 are hermetically sealed from the battery and/or a capacitor of the device. In addition, various features, such as the ribs and steps discussed above relative to the other embodiments, can be added to any of the main surfaces 113/115/118 in order to further define component cavities within chambers 120/122.

Because intermediate portion 106 includes wall 116, which in one embodiment is substantially parallel with portions of walls 112 and 114, it is readily welded together with first and second housing portions 102 and 104 along first and second connecting lines 126 and 128. As such, intermediate portion 106 provides an easily assembled structure that both provides a hermetic seal between first and second chambers 120 and 122 and also affords ready access to first and second connecting lines 126 and 128 thereby insuring the overall housing 100 can be welded together and maintain hermeticity between its interior and its exterior.

In one embodiment, each of first and second housing portions 102 and 104 and intermediate portion 106 are formed using additive manufacturing processes, such as metal injection molding (MIM), direct metal laser sintering (DMLS), stereolithography (SLA), or three-dimensional printing (3D printing). In another embodiment, intermediate portion 106 is formed using additive manufacturing processes, while first and second housing portions 102 and 104 are formed using conventional techniques, such as stamping or SPF. Even with first and second housing portions 102 and 104 formed with conventional techniques, and accordingly not including integrated features, housing 100 can still be provided with features where intermediate portion 106 is formed using additive manufacturing processes. Because intermediate portion 106 is formed using additive manufacturing processes, wall 116 is readily formed to mate with walls 112 and 114 of first and second housing portions 102 and 104. Similarly, ribs, such as those illustrated in 2A-3B are readily added to either side (or both) of main surface 118 of intermediate portion 106 in order to create the component cavities, such as described and illustrated in FIGS. 2A-3B.

FIGS. 5A-5D illustrate alternative embodiments of housings 150/180/210/240 including various features. FIGS. 5A-5D are cross-sectional illustrations of housings 150/180/210/240, including first housing portions 152/182/212/242, second housing portions 154/184/214/244 and intermediate portions 156/186/216/246. Housings 150/180/210/240 are similar to housing 100 described above, and accordingly, in one embodiment, each of first and second housing portions 152/182/212/242 and 154/184/214/244 and intermediate portions 156/186/216/246 can be formed using additive manufacturing processes, or intermediate portions 156/186/216/246 can be formed using additive manufacturing processes, while first and second housing portions 152/182/212/242 and 154/184/214/244 are formed using conventional techniques.

As with the housing 100 above, housings 150/180/210/240 are each implantable medical devices in which intermediate portions 156/186/216/246 are positioned between first and second housing portions 152/182/212/242 and 154/184/214/244, such that when first housing portions 152/182/212/242 are sealed to intermediate portions 156/186/216/246 on a first side and second housing portions 154/184/214/244 is sealed to intermediate portions 156/186/216/246 on a second side opposite the first, the inside of each of housings 150/180/210/240 is fully hermetically sealed relative to its outside. Furthermore, in some embodiments, intermediate portions 156/186/216/246 divides each of housings 150/180/210/240 internally into two separate chambers. As with housing 100, each of first portions 152/182/212/242 include walls 162/192/222/252, each of second portions 154/184/214/244 include walls 164/194/224/254 and each of intermediate portions 156/186/216/246 include walls 166/196/226/256. Each of walls 162/164/166, 192/194/196, 222/226/224, and 252/254/256 are readily welded to each other to seal housings 150/180/210/240, such that its inside is sealed relative to its outside.

In addition, each of intermediate portions 156/186/216/246 also include further features useful in some applications. For example, intermediate portion 156 in FIG. 5A includes back-up bands 158 positioned adjacent walls 162, 164, and 166. In order to hermetically seal housing 150, first housing portion 152 is welded to intermediate portion 156 and second housing portion 154 is welded to intermediate portion 156. Back-up bands 158 allow added protection within housing 150, especially for electronics and other sensitive components contained within housing 150. Because the back-up bands 158 run laterally along walls 162, 164, and 166 inside housing 150, they are between the weld source and the housing interior and accordingly provide interference or protection to electronics and other sensitive components within the housing 150 as first and second housing portions 152 and 154 are welded to intermediate portion 156 in the area of back-up bands 158. Similar back-up bands 217 are illustrated in FIG. 5C. Also, intermediate portions 186 and 246 in FIGS. 5B and 5D have stepped features 189/249 located similarly that also function as back-up bands to add some protection for internal electronics and other sensitive components.

Figure 5A:
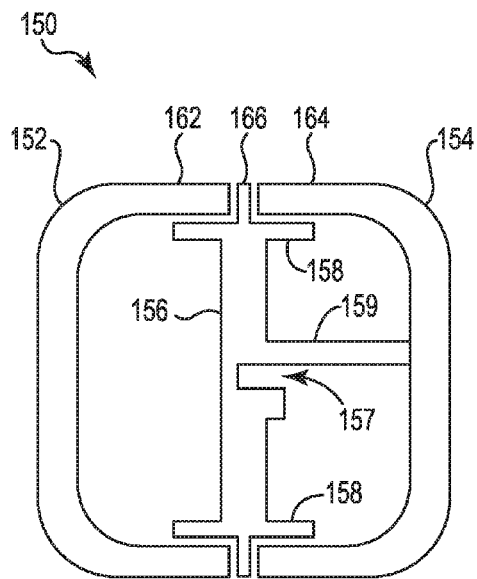
FIGS. 5A-5D illustrate sectional views of a housing for an implantable medical device in accordance with various embodiments.
Figure 5B:
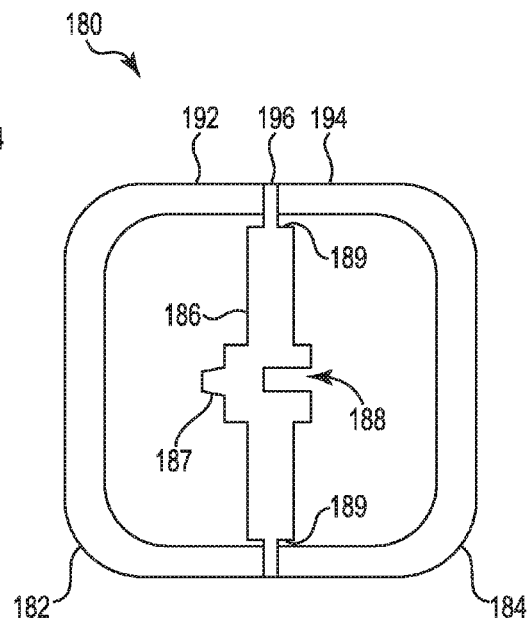
Figure 5C:
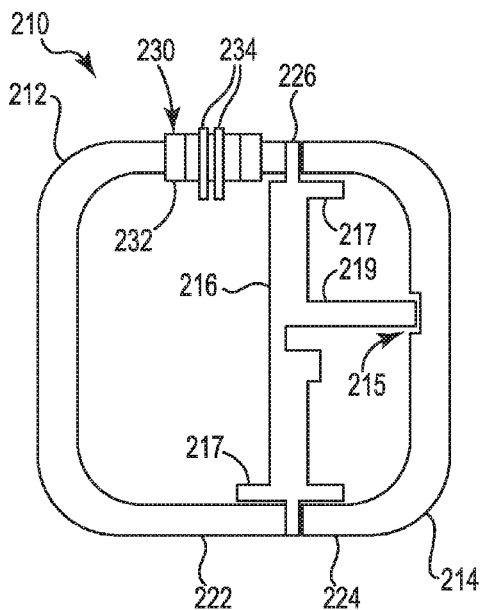

In one embodiment, intermediate portions 156 and 216 in FIGS. 5A and 5C further include features such as standoffs 159/219 and recesses 157/215, which are useful in some applications. During assembly of housings 150/210, standoffs 159/219 and recesses 157/215 can be useful in locating internal components, provide support and further define component cavities. For example, standoffs 159/219 can provide lateral support for intermediate portions 156/216 as they contact second housing portions 154/214, thereby supporting intermediate portions 156/216 against the housing. Also, standoffs 159/219 can further divide the inside of housings 150/210 into separate sections, such as further component cavities.

Also, recess 157 of FIG. 5A can be configured to accept a component that fits uniquely into the recess 157 such that an assembler, or a placement machine in the case of automated assembly, can readily place the component in the correct location within housing 150. Also, recess 215 of FIG. 5C can be located uniquely to allow standoff 219 to be accurately placed by having it fit into recess 215. This will also facilitate ease in assembly and help avoid mistakes in aligning parts during assembly. Furthermore, intermediate portion 186 in FIG. 5B includes features such as recess 188 and knuckle 187, each of which also are helpful in assembling housing 180 and ensuring accurate placement of components within the housing 180.

Figure 5D:
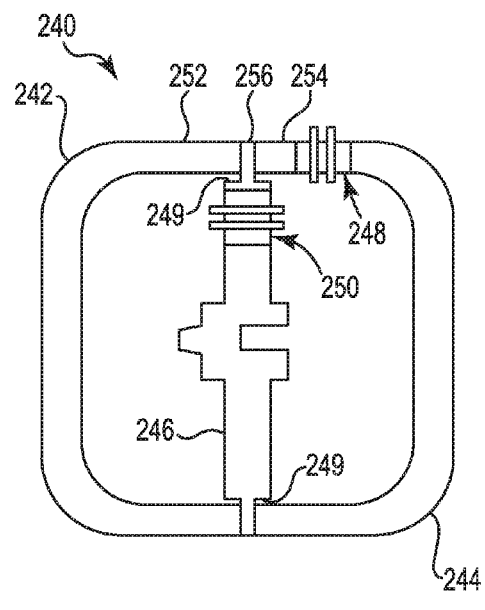

In one embodiment, one or more of the housing portions and intermediate portions include features such as feedthroughs 230/248/250 as illustrated in FIGS. 5C and 5D. For example, feedthrough 230 is located in first housing portion 212, and provides conductive access between the inside of housing 210 and its outside while still maintaining hermeticity therebetween. In one embodiment, feedthrough 230 includes an insulative portion 232 and conductors 234 passing through insulative portion 232. Insulative portion 232 is nonconductive and maintains a hermitic seal relative to the adjacent housing portion 212. Conductors 234 are electrically conductive and pass through the insulative portion 232 and also maintain a hermitic seal relative to the adjacent insulative portion 232. Conductors 234 allow electrical connectivity between components within housing 210 to those outside housing 210 while maintaining hermeticity therebetween.

Feedthroughs 248 and 250 are similarly configured and illustrated in FIG. 5D. Feedthrough 248 is located in second housing portion 244, and provides conductive access between the inside of housing 240 and its outside while still maintaining hermeticity therebetween. Feedthrough 250 is located in intermediate portion 246, and provides conductive access between two internal chambers of housing 240 on either side of intermediate portion 246, while still maintaining hermeticity therebetween.

In each case, feedthroughs 230/248/250 are features formed as part of forming the respective portions in which they reside, first housing portion 212, second housing portion 244, and intermediate portion 246. With the additive manufacturing processes used for forming the various portions, these features are readily integrated into the portions.

In fact, because the above-described housing portions and intermediate portions, including the various above-described features, such as back-up bands, recesses, standoffs, feedthroughs, etc. are formed with additive manufacturing, such MIM, DMLS, SLA, or 3D printing, each of these above-describes features are integrally formed as part of forming the housing portions or the intermediate portions. This leads to fewer number of components required for these types of products and easier and faster assembly of the portions to form the overall product, lowering errors and reducing cost.

Figure 6:
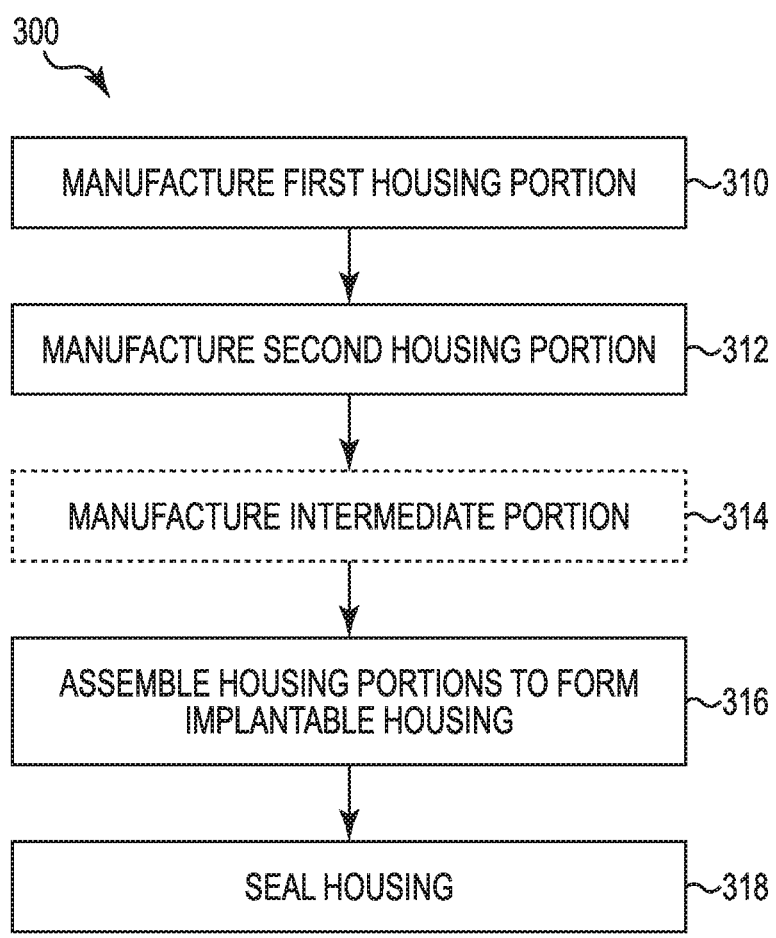
FIG. 6 illustrates a process for manufacturing an implantable medical device in accordance with one embodiment.

FIG. 6 illustrates a process 300 for manufacturing an implantable medical device, such as described above with respect to FIGS. 1-5D. In one embodiment, a first housing portion is manufactured at step 310. In some embodiments, a first housing portion, such as first housing portions 16/102/152/182/212/242, is formed using additive manufacturing, such MIM, DMLS, SLA, or 3D printing. In such cases, forming of the first housing portion includes integrally forming features included in the housing portion, such as walls, ribs, component cavities, standoffs, back-up bands and so forth.

For example, in the case of MIM, such features are built into the mold parts before the metal is injecting in, such that the features are integrally molded into the housing portion. In the case of 3D printing, the printing is controlled such that the features are printed with the housing portion such that the features are integrally formed with the housing portion. In some embodiments, forming the first housing portion includes forming at least one component cavity, such as first component cavity 40 illustrated in FIGS. 2A and 2C integrally into first housing portion.

In some embodiments, such as where an intermediate portion with features is used, such as illustrated in FIG. 4A, the first housing portion can also be formed by conventional means, such as stamping or SPF.

In one embodiment, a second housing portion is manufactured at step 312. In some embodiments, a second housing portion, such as second housing portions 18/104/154/184/214/244, is formed using additive manufacturing, such MIM, DMLS, SLA, or 3D printing. In such cases, forming of the second housing portion includes integrally forming features included in the housing portion, such as walls, ribs, component cavities, standoffs, back-up bands and so forth, just as described above for the first housing portion. In other embodiments, such as where an intermediate portion with features is used, such as illustrated in FIG. 4A, the second housing portion can also be formed by conventional means, such as stamping or SPF.

In some embodiments, an intermediate portion is manufactured at step 314. In some embodiments, such as illustrated in FIG. 1, an intermediate portion is not used, and in such case step 314 is optional. When the intermediate portion is used, the intermediate portion, such as intermediate portions 106/156/186/216/246, is formed using additive manufacturing, such MIM, DMLS, SLA, or 3D printing. In such cases, forming of the intermediate portion includes integrally forming features as part of the intermediate portion.

At step 316, the housing portions are assembled to form an implantable device, such as implantable medical device 10. Where only first and second housing portions have been formed, various components are first placed on first and/or second housing portions. Where an intermediate portion is formed, various components may also be place on the intermediate portion as will. In either case, features, such as ribs, walls, component cavities, standoffs, recesses, knuckles, back-up bands, etc., which are integrated into first and second housing portions and into the intermediate portion are used to facilitate placement of the various components that will ultimately be sealed within the housing. Components such as electronic circuit boards, batteries and capacitors can fit into cavities and other recesses that are formed by the features that are integrated into the first and second housing portions and the intermediate portion. In some cases, lids may then seal some of these components, such as batteries and capacitors as previously discussed, into one of the housing portions. The assembly of the components can be by hand or with automation and placement is aided by the features present in the housing portions.

Next, at step 318, the housing portions are brought together, such as illustrated in FIG. 1, and then the housing portions are sealed together to form the housing and hermetically seal the components within the housing. In one embodiment, in order to hermetically seal the housing, a laser weld is used along the interface between the first and second housing portions, such as along connecting line 20 in FIG. 1.

Where a first and second housing portion and an intermediate portion are formed, all three portions are connected, such as illustrated in FIGS. 4A and 4B. For example, first housing portion 102 is welded to intermediate portion 106 along second connecting line 128 and second housing portion 104 is welded to an opposite side of intermediate portion 106 along first connecting line 126 (as illustrated in FIG. 4B). Similarly, sealing the portions this way hermetically seals the components within the housing relative to its exterior.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A housing for an implantable medical device comprising:
    a first housing portion comprising metal;
    an intermediate portion comprising metal and having first and second sides opposite one another and having integrated features; and
    a second housing portion comprising metal;
    wherein the first housing portion is sealed to the first side of the intermediate portion and the second housing portion is sealed to the second side of the intermediate portion thereby forming an housing internal space within first and second housing portions and containing the intermediate portion and its features, such that the features are hermetically sealed within the housing relative to an external space that is outside the housing.

2. The housing of claim 1, wherein the features comprise at least one of a group comprising walls, ribs, component cavities, standoffs, recesses, knuckles, and back-up bands.

3. The housing of claim 1, wherein the intermediate portion defines a first chamber between the first housing portion and the intermediate portion and a second chamber between the second housing portion and the intermediate portion.

4. The housing of claim 3, wherein the first and second chambers are hermetically sealed from each other by the intermediate portion.

5. The housing of claim 1, wherein the first housing portion and the second housing portion are each characterized by the absence of features, such that they can be formed from stamping.

6. The housing of claim 1, wherein the first and second housing portions and intermediate portion each comprise wall sections configured about each respective periphery and configured immediately adjacent each other on the housing, the wall sections of the first housing portion and the intermediate portion forming a first connection line and the wall sections of the second housing portion and the intermediate portion forming a second connection line, wherein the portions are readily joined along the first and second connection lines.

7. The housing of claim 6, wherein the intermediate portion comprises a back-up band adjacent one of the first and second connection lines, the back-up band configured to protect components within the housing when the housing is welded along the first or second connection lines.

8. The housing of claim 6, wherein at least one of the intermediate portion and first and second housing portions comprise a feature configured to accept a component that fits uniquely into the feature, such that an assembler or placement machine, can place the component in the correct location within the housing.

9. The housing of claim 1, wherein the first and second housing portions and intermediate portion comprise one of Ti 6Al-4V (Grade 5 titanium), Ti 6Al-4V ELI (Grade 23 titanium), and Ti 3Al 2.5V (Grade 9 titanium).

10. A housing for an implantable medical device comprising:
    a first housing portion comprising metal and having features integrated in the first housing portion;
    a second housing portion comprising metal; and
    an intermediate portion between the first and second housing portions, the intermediate portion defining a first chamber between the first housing portion and the intermediate portion and a second chamber between the second housing portion and the intermediate portion;
    wherein the first and second housing portions are each sealed to the intermediate portion such that each of the first and second chambers are hermetically sealed relative to an external space outside the housing and such that the features are sealed within the first chamber.

11. The housing of claim 10, wherein the first and second housing portions and intermediate portion each comprise wall sections configured about each respective periphery and configured immediately adjacent each other on the housing, the wall sections of the first housing portion and the intermediate portion forming a first connection line and the wall sections of the second housing portion and the intermediate portion forming a second connection line, wherein the portions are readily joined along the first and second connection lines.

12. The housing of claim 10, wherein the intermediate portion comprises a back-up band adjacent one of the first and second connection lines, the back-up band configured to protect components within the housing when the housing is welded along the first or second connection lines.

13. The housing of claim 10, wherein the integrated features comprise at least one of a group comprising walls, ribs, component cavities, standoffs, recesses, knuckles, and back-up bands.

14. The housing of claim 10, wherein the first chamber and the second chamber are hermetically sealed relative to each other by the intermediate portion.

15. The housing of claim 10, wherein the first and second housing portions comprise one of Ti 6Al-4V (Grade 5 titanium), Ti 6Al-4V ELI (Grade 23 titanium), and Ti 3Al 2.5V (Grade 9 titanium).

* * * * *